United States Patent [19]

Arias

[11] Patent Number: 4,701,446
[45] Date of Patent: Oct. 20, 1987

[54] PYRETHROID CONTAINING PHARMACEUTICAL COMPOSITIONS

[75] Inventor: Jose A. Arias, Mexico, Mexico

[73] Assignee: T & R Chemicals, Inc., Clint, Tex.

[21] Appl. No.: 595,360

[22] Filed: Mar. 30, 1984

[30] Foreign Application Priority Data

Mar. 31, 1983 [GB] United Kingdom ............... 8308974

[51] Int. Cl.$^4$ ..................... A01N 65/00; A01N 27/00
[52] U.S. Cl. .................................. 514/65; 514/762; 514/895; 424/127
[58] Field of Search .................... 514/65, 762, 895; 424/153, 127

[56] References Cited

U.S. PATENT DOCUMENTS 4,100,297  7/1978  Grandadam et al. .

FOREIGN PATENT DOCUMENTS 447949  5/1935  United Kingdom .
2072013  9/1981  United Kingdom .

OTHER PUBLICATIONS

Chemical Abstracts 7755, p. 1033.
"Plantes Medicinales Des Regions Temperees" by Bezanger-Beauquesene, pp. 390-392.
Official Action from New Zealand Patent Office of Jan. 27, 1986.
"The Merck Manual of Diagnosis and Therapy", 1982.
Veterinary Bulletin, Commonwealth Agricultural Bureau, CAB 83A17373, V. K. Stubbs, et al.: "Cyhalothrin—a Novel Acaricidal and Insecticidal Synthetic Pyrethroid for the Control of the Cattle Tick (Boophilis Microplus) and the Buffalo Fly Haematobia Irritans Exigua", abstract.
Bezanger-Beauquesne et al.: "Plantes Medicinals des Regions Temperees", 1980, pp. 390-439, Chrysanthemum . . . , Maloine S. A., Paris (no translation).
Chemical Abstracts, vol. 53, No. 5, Mar. 1959, column 4570, No. e, Taylor et al.: "The Isolation and . . . ", Can. Pharm. J., Sci. Sect. 91, 309-111 ('85) abstract.
Chemical Abstracts 80 30695z.
Chemical Abstracts 87 111394x.
Chemical Abstracts 96 159266v.
Chemical Abstracts 98 119212j.
Chemical Abstracts 98 149467p.
Bezanger-Beauquesne: Plantes Medicinales et Phytotherapie, 1969, Tome III, No. 4, pp. 296-309, "Chrysanthemes Insecticides".
Bezanger-Beauquesne: Plantes Medicinales et Phytotherapie, 1982, Tome XVI, No. 3, pp. 206-229, "Plantes Superieures Antitumorales" (not translated).
Chemical Abstracts 74 102985v.
Chemical Abstracts 75 725464.
Chemical Abstracts 78 119955r.

Primary Examiner—Johnnie R. Brown
Assistant Examiner—John W. Rollins
Attorney, Agent, or Firm—Nixon & Vanderhye

[57] ABSTRACT

Parasitic and viral diseases are treated with a pyrethroid preferably in the presence of alpha-pinene. Preferred compositions are extracts of pyrethrum with water, aqueous ethyl alcohol, or alpha-pinene.

15 Claims, No Drawings

PYRETHROID CONTAINING PHARMACEUTICAL COMPOSITIONS

FIELD OF THE INVENTION

The present invention relates to the treatment of parasitic and, especially, viral diseases with a pyrethroid. It provides certain oral pharmaceutical compositions containing a pyrethroid, for treating a parasitic or viral disease.

BACKGROUND OF THE INVENTION

The pyrethroids include naturally occurring and synthetic esters of chrysanthemummonocarboxylic acid (i.e. 2,2-dimethyl-3-(2'-methylpropenyl)-cyclopropanecarbox ylic acid) or chrysanthemumdicarboxylic acid (i.e. 2,2-dimethyl-3-(2'-carboxypropenyl)cyclopropanecarboxylic acid) and are widely used as insecticides. The most important naturally occurring pyrethroids are Pyrethrin I and II which are the major active insecticidal principles of pyrethrum. Pyrethrin I is the pyrethrolone (i.e. 4-hydroxy-3-methyl-2-(2', 4'-pentadienyl)-2-cyclopenten-1-one) ester of chrysanthemummonocarboxylic acid and Pyrethrin II is the pyrethrolone 3-ester of chrysanthemumdicarboxylic acid-1-methyl ester. Pyrethrum also contains as minor active insecticidal principles Cinerin I and Cinerin II, which are the 4-hydroxy-3-methyl-2-(2'-butenyl)-2-cyclopenten-1-one esters of chrysanthemummonocarboxylic acid and chrysanthemumdicarboxylic acid-1-methyl ester respectively. Pyrethroids have low mammalian toxicity because they are relatively easily metabolized by warm-blooded animals and hence have found widespread acceptance as insecticides.

Some medical uses have been proposed for certain pyrethroids but, to the best of our knowledge, the majority of such uses have been directly related to their known insecticidal properties. The medical uses presently known to us are briefly acknowledged below.

Pyrethrum has been used as an active ingredient in an ointment for the treatment of scabies, which is a contagious skin infection caused by the mite Sarcoptes scaboi (see The Merck Index, Eighth Edition, 1968). Further, pyrethrum has been used in insect repellent creams (see the Extra Pharmacopoeia, Martindale, Twenty-fourth Edition, 1958) and in external preparations for the treatment of body lice, especially head lice (see "A 200 Pyrinate" and "Rid", The Physicians Desk Reference 1982). In this connection, UK Patent Specification No. 2072013 (published 1981) describes improving the activity of pyrethroids in the treatment of body lice by using them in conjunction with vegetable oils and/or detergents.

It has been proposed to use certain synthetic pyrethroids in the veterinary treatment of various forms of mange and ticks by oral, parenteral and topical routes (see U.S. Pat. No. 4100297 issued 1978).

It was proposed in 1936 (see UK Patent Specification No. 447949) to use a pyrethrum containing composition in the treatment of gonorrhoea and dental suppurating diseases. The composition comprises a petroleum ether, or similar, extract of pyrethrum together with perilla aldehyde in an organic solvent. The perilla aldehyde was obtained from oil of perilla treated so as to eliminate limonene and pinene and other impurities. We understand that oil of perilla is obtained from a type of mint plant.

More recently (1959), it has been reported that pyrethrin extracts of Chrysanthemium cinerariaefolium have muscle relaxant properties as tested using guinea pig and rat ileum (see Chemical Abstracts, 53, 4570f).

Surprisingly, it has been found that pyrethroids are effective at low doses in the treatment of a wide range of parasitic and viral diseases in humans, including amoebiasis, genital herpes, hepatitis, influenza, malaria and parotitis (mumps).

SUMMARY OF THE INVENTION

According to a first aspect of this invention, disclosed is a method of treating diseases, such as amoebiasis, malaria and trichomoniasis, in which an effective amount of a pyrethroid is orally administered. Preferably the amount administered is in the range of 0.0001 to 1 mg/kg body weight at a frequency of one to four times daily.

According to a second aspect of this invention, disclosed are pharmaceutical compositions intended for oral administration, in unit dosage form, that consist essentially of a pyrethroid in admixture or otherwise associated with a pharmaceutically acceptable carrier or diluent. Preferably each unit dose contains from 0.0005 mg to 5 mg of the pyrethroid. These pharmaceutical compositions are particularly useful in treating diseases in humans.

DETAILED DESCRIPTION OF THE INVENTION

Pyrethroids are useful in the treatment of parasitic and viral diseases, especially, but not exclusively, amoebiasis, genital herpes, hepatitis, influenza, malaria and parotitis (mumps). Other parasitic diseases which are expected to respond to such treatment include trichomoniasis. Other viral diseases which are expected to respond to treatment with a pyrethroid include common cold, and herpes simplex and zoster infections.

The pyrethroid can be any naturally occurring or synthetic ester of chrysanthemummonocarboxylic acid or chrysanthemumdicarboxylic acid which is non-toxic and otherwise pharmacologically acceptable at the dosages employed. However, the presently preferred pyrethroids for use in the present invention are those derived from pyrethrum, namely Cinerin I and II and, especially, Pyrethrin I and II. Pyrethrum itself can be used but it is presently especially preferred that the pyrethroid should be obtained by extracting pyrethrum with water, ethyl alcohol or, most preferred, with alpha-pinene. The alpha-pinene can be in the form of Mexican, or other, turpentine containing at least 80% alpha-pinene. Usually, the said preferred pyrethroid will be used in the form of a solution in water, aqueous alcohol or, especially, alpha-pinene.

In connection with the above, it appears that alpha-pinene exerts a synergistic effect on pyrethroids enhancing their activity in treating protozoal and viral diseases. Accordingly, it is a preferred feature of the present invention that alpha-pinene is administered concomitantly with the pyrethroid, advantageously in the same composition.

It is also preferred that an alkali metal bisulphite, especially sodium metabisulphite, is present in the composition of the invention.

It is particularly preferred that both alpha-pinene and the bisulphite are contained in the composition of the invention.

The pyrethroids are administered orally to achieve the desired effect. They can be administered alone or in the form of pharmaceutical preparations to the patient being treated. The amount of compound administered will vary and can be any effective amount. Depending upon the patient and the pyrethroid, the quantity of pyrethroid administered may vary over a wide range to provide, for example, from about 0.0001 mg/kg to about 1 mg/kg, usually about 0.01 to about 0.1 mg/kg, of body weight of the patient per dose. Unit doses of pyrethroid can contain, for example, from about 0.0005 mg to about 5 mg, usually about 0.01 to about 1 mg, of the pyrethroid and may be administered, for example, from 1 to 4 times daily.

It will be appreciated that the dosage levels referred to above are substantially less than those envisaged in U.S. Pat. No. 4100297 for internal administration of certain pyrethroids for the treatment of acarids. The lowest dose specified in the U.S. Patent is 3 mg/kg.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as one or more drops or a 5 ml (teaspoon) quantity of a liquid or a half or quarter of a scored tablet, of the multiple dose form.

In the composition aspect of the invention there are provided pharmaceutical compositions in which form the pyrethroids will normally be utilized. Such formulations are prepared in a manner well known per se in the pharmaceutical art and usually comprise at least one pyrethroid in admixture or otherwise in association with a pharmaceutically acceptable carrier or diluent thereof. For making those formulations the active ingredient usually will be mixed with a carrier, or diluted by a diluent, or enclosed or encapsulated in a capsule, sacket, cachet, paper or other container. The carrier or diluent may be solid, semi-solid or liquid material which serves as a vehicle, excipient or medium for the active ingredient. Suitable carriers or diluents are well known per se. As indicated above, it is presently preferred that the pyrethroid is administered as a solution in a suitable liquid carrier such as water or, preferably, aqueous alcohol or, especially, alpha-pinene. When administered as a solution, the concentration of pyrethroid usually will be in the range 0.001 to 1, especially 0.01 to 0.5, percent by weight based on the liquid carrier.

The compositions of the invention are adapted for enteral use and may be administered to the patient in the form of tablets, capsules, solutions, suspensions or the like.

One preferred composition of the invention comprises a solution of 0.001 to 1.0, preferably 0.1 to 0.5, percent by weight pyrethroid in alpha-pinene preferably containing up to 11% sodium metabisulphite. A particularly preferred example of said composition is obtained by macerating dried pyrethrum flowers for, for example, 30 days in Mexican turpentine optionally containing sodium metabisulphite and then filtering off the solids content.

Another preferred composition of the invention comprises a solution of 0.001 to 1.0, preferably 0.1 to 0.5, percent by weight pyrethroid in aqueous ethyl alcohol preferably containing up to 11% sodium metabisulphite.

Suitably, the aqueous alcohol contains 25 to 35% ethyl alcohol. A particularly preferred example of said composition is obtained by homogenizing an ethyl alcohol extract of dried pyrethrum flowers with aqueous ethyl alcohol optionally in the presence of sodium metabisulphite.

The invention is further illustrated in the following Examples.

EXAMPLE 1

Mexican gum turpentine (specific weight 860.5, 80% minimum alpha-pinene content) (1 liter) is slowly added to a sodium metabisulphite (105 gms) in a 1.5 liter vessel. The vessel is closed and stirred gently for 10 minutes. Chrysanthemum powder (110 gms, 1.2% concentration) is added and the mixture stirred every 6 days. The mixture is left to macerate for 30 days with occasional stirring and then the solids filtered off. The filtrate (identified as "V-1") is stored in dropper bottles for administration at a dose of 1 drop orally per 10 kg body weight of patients suffering from a parasitic or viral infection.

V-1 has been found to be effective against type A hepatitis (infectious hepatitis) and type B hepatitis (serum hepatitis) at doses of 1 drop orally per 10 kg body weight twice daily. A clinic treated 7 cases of acute hepatitis in patients in which the main symptoms and signs were anorexia, extreme fatigue (which made it impossible to attend school or work), moderate temperature (38° C.), cephalalgia and poor condition in the hepatic area, choluria, hepatomegaly, icteric conjunctivitis, hypocholia, acholia, splenamegaly and ascites. In laboratory tests, bilirubin, glutaminase and oxalacetic, alkaline phosphatase, lactic dehydrogenase quantities were considerably increased. The patients were given V-1, in relation to their weight and their symptoms and signs diminished gradually until complete recovery after 10 to 12 days.

The clinic also successfully treated 2 cases of chronic hepatitis caused by type B virus. One was a boy, age 5, who presented most of the symptoms and signs above stated as well as the altered laboratory tests. In this case 25 days were needed for complete recovery.

Sample clinical results of treatment of hepatitis with V-1 are provided in Example 4.

Further, the clinic successfully treated amoebiasis, genital herpes, and malaria with V-1 and sample clinical results are provided in Examples 2, 5 and 3 respectively.

EXAMPLE 2

Sample Clinical Results (V-1)—Amoebiasis

| PATIENT 2A | |
| --- | --- |
| Male: | |
| Age: | 6 years |
| Weight: | 20 Kgs. |
| Temperature: | 36.5° C. |

Principal symptoms and signs:

Anorexia, sometimes shivering fits and general feeling of illness which could be defined with precision. Thereafter there were diarrhoeial evacuations with mucus, blood and very foetid odour in great quantity and with a frequency of 4 evacuations per day. This continued for 3 days, appeared again in 8 days with the evacuations having the same characteristics as described above and accompanied, on some occasions, by a fever of 38° C., nausea and vomiting of the gastric contents. Patient referred to abdominal pain upon touching and where there was slight abdominal distention.

Diagnosis

Acute intentinal amoebiasis

Treatment 5 drops V-1 orally twice a day

Result

Complete recovery after 10 days treatment.

| PATIENT 2B | |
|---|---|
| Male: | |
| Age: | 6 years |
| Weight: | 19 Kgs. |
| Temperature: | 36.5° C. |

Principal symptoms and signs:

The patient complained of cramp pains localized in the left iliac fossa, painful to the touch, flatulence, and with disorders of the intentinal evacuations, which then were presented in the form of diarrhoeia with mucus and sometimes blood preceded by tenesmus, with a frequency of 4 to 5 times per day. These evacuations lasted 3 days and returned each 8 days having the same characteristics as set out above.

Diagnosis:

Acute intentinal amoebiasis.

Treatment 5 drops V-1 orally twice a day

Result

Complete recovery after 8 days treatment.

| PATIENT 2C | |
|---|---|
| Male: | |
| Age: | 35 years |
| Weight: | 70 Kgs. |
| Temperature: | 36.5° C. |
| T.A. | 140/80 |

Principal symptoms and signs:

Diarrhoeial evacuations, intentinal colic, nausea, vomiting and rectal tenesmus which accompanied defecation. The patient displayed anorexia and shivering fits and this condition lasted from 3 to 5 days with renewed appearance of intentinal colic with pasty evacuations, semiliquid, of foetid smell, with mucous and sometimes with blood and remains of intentinal mucous and which was accompanied by rectal tenesmus having a frequency of 6 to 8 evacuations per day. Generally poor state, anorexia, asthenia and acratia.

Diagnosis

Acute intestinal amoebiasis.

Treatment 8 drops V-1 orally three times of day

Result

Complete recovery after 15 days treatment.

| PATIENT 2D | |
|---|---|
| Female: | |
| Age: | 6 years |
| Weight: | 21 Kgs. |
| Temperature: | 36.5° C. |

Principal symptoms and signs:

Anorexia, nausea, and sometimes vomiting with diarrhoeial evacuations which are abundant and semiliquid and were accompanied by blood and with a frequency of 6 times per day. The evacuations lasted 4 days on average and were repeated each 3 days becoming more intense and accompanied by abdominal pain.

Diagnosis

Acute intestinal amoebiasis.

Treatment 5 drops V-1 orally twice a day.

Result

Complete recovery after 7 days treatment.

| PATIENT 2E | |
|---|---|
| Male: | |
| Age: | 4 years |
| Weight: | 16 Kgs. |
| Temperature: | 36.5° C. |

Principal symptoms and signs:

Intestinal colic, nausea, and sometimes vomiting preceded by semiliquid diarrhoeial evacuations, of pasty form and with mucous and with remains of food and which are accompanied by rectal tenesmus and with a frequency of 5 evacuations per day. Further, he was generally in poor condition with anorexia, asthenia and acratia.

Diagnosis

Acute intestinal amoebiasis.

Treatment 5 drops V-1 orally twice a day.

Result

Complete recovery after 8 days treatment.

| PATIENT 2F | |
|---|---|
| Male: | |
| Age: | 4 years |
| Weight: | 16 Kgs. |

Principal symptoms and signs:

The patient had anorexia, asthenia, and slight acratia and there were diarrhoeial evacuations with mucus, blood and the remains of food, accompanied by tenesmus and presented with a frequency of 4 evacuations per day which lasted 3 days, repeated in 5 days with the same characteristics as noted above. Abdominal distention and pain upon touching the left iliac fosse.

Diagnosis

Acute Intestinal amoebiasis

Treatment 5 drops V-1 orally twice a day.

Result

Complete recovery after 7 days treatment

EXAMPLE 3

Sample Clinical Reports (V-1)—Malaria

| PATIENT 3A | |
|---|---|
| Male: | |
| Age: | 30 years |
| Weight: | 70 Kgs. |
| T.A.: | 120/70 |
| Temperature: | 38° C. |

Principal symptoms and signs:

Fever of 38° to 39° C. with general poor condition, with asthenia, acratia and anorexia, and with loss of weight (unquantified). Slight diaphoresis, intense frontal Cephalalgia and extreme debility. Hepatomegalia Grade 2 painfull to the touch and slight splenomegalia +. The patient complained of myalgia and arthrosis of variable intensity.

Diagnosis

Malaria

Treatment 8 drops V-1 orally twice a day

Result

Complete recovery after 8 days treatment.

| PATIENT 3B | |
|---|---|
| Male: | |
| Age: | 32 years |
| Weight: | 76 Kgs. |
| T.A.: | 130/70 |
| Temperature: | 39° C. |

Principal symptoms and signs:

Intermittent fever preceded by intense shivering fits which from time to time shook the patient and the duration of which was approximately from 4 to 6 hours. Intense cephalalgia which did not cease with treatment with analgesics, tachycardia, oliguresis and dry mouth. Hepatomegalia ++, anaemia Grade 1 and slight splenomegalia.

Diagnosis

Malaria

Treatment 8 drops V-1 orally twice a day

Result

Complete recovery after 12 days treatment.

| PATIENT 3C | |
|---|---|
| Male: | |
| Age: | 30 years |
| Weight: | 69 Kgs. |
| T.A.: | 140/80 |
| Temperature: | 39° C. |

Principal symptoms and signs:

Intermittent fever (unquantified) preceded by intense shivering fits, the mean duration of which was 8 hours approximately and which disappeared in the form of intense diaforesis. Hypothermia, intense frontal cephalalgia, arthralgia, anorexia, asthenia and acratia accompanied by loss of weight (unquantified).

Diagnosis

Malaria

Treatment 8 drops V-1 orally twice a day

Result

Complete recovery after 8 days treatment.

| PATIENT 3D | |
|---|---|
| Male: | |
| Age: | 52 years |
| Weight: | 77 Kgs. |
| T.A.: | 150/80 |
| Temperature: | 39° C. |

Principal symptoms and signs:

Intermittent fever (unquantified) precided by shivering fits, the mean duration of which was three hours after which they disppeared in the form of intense diaforesis. Hypothermia, cephalalgia, thirst, asthenia, and acratia. Anaemia grade 1, hepatomegalia ++, splenomegalia + which were painful to the touch. The skin of the patient was dry and hot, with reddening of the face and with very high temperatures (up to 40° C.) General poor condition accompanied by intense fatigue and debility.

Diagnosis

Malaria

Treatment 8 drops V-1 orally twice a day

Result

Complete recovery after 15 days treatment.

| PATIENT 3E | |
|---|---|
| Male: | |
| Age: | 38 years |
| Weight: | 77 Kgs. |
| T.A.: | 130/90 |
| Temperature: | 39° C. |

Principal symptoms and signs:

Intermittent fever accompanied by intense shivering fits with a duration of approximately 6 hours and which disppeared in the form of diaphoresis which was very intense and which from time to time led to saturation of the clothing of the patient, and which left the patient without symptoms and very debilitated. The fever occurred the following day and reached 40° C. and was accompanied by intense cephalalgia, myalgia, arthralgia, oliguresis and bad general state.

Diagnosis

Malaria

Treatment 9 drops V-1 orally twice a day

Result

Complete recovery after 20 days treatment.

EXAMPLE 4

Sample Clinical Results—Heptatis

| PATIENT 4A | |
|---|---|
| Male: | |
| Age: | 30 years |
| Weight: | 63 Kgs. |
| T.A.: | 110/70 |
| Temperature: | 39° C. |

Principal symptoms and signs:

Alcoholism since 18 years of age (taken twice a week to achieve complete intoxication). Anorexia, generally poor condition, vomiting of the contents of the stomach during which there appear joint pains of variable intensity which are accompanied by choluria and acholia. This condition lasted three days and was followed by generalized icteric conjunctivitis ++. Generalized abdominal pain, as well as hepatomegalia Grade ++, and abdominal distention. Fever 39° C., with Asthenia, acratia and anorexia.

Diagnosis

Acute (infectious) Viral Hepatitis.

Treatment 7 drops V-1 orally twice a day

Result
Complete recovery after 21 days treatment.

| PATIENT 4B | |
|---|---|
| Female: | Age: 5 years |
| Weight: 18 Kgs. | Temperature: 38° C. |

Principal symptoms and signs:

From three years of age had diarrhoeial evacuations with mucus and blood with a frequency of twice per week. Anorexia, asthenica, and acratia which was accompanied by cephalalgia, a fever of 38° C. and generally poor condition which lasted three days after which there appeared choluria, hypocholia and acholia, as well as icteric conjunctivities. Slight hepatomegalia $+$ and slight splenomegalia $+$. Fever at 38° C., asthenia, acratia, anorexia which was accompanied by attacks on the general health.

| Bilirubina: | direct 6 mg/100 ml |
| | indirect 5 mg/100 ml |
| lactic dehydrogenase 815 mU/ml | |
| Transaminase: | glutamic - pyruvic 22 mU/ml |
| | glutamic - oxalacetic 26 mU/ml |
| alkaline phosphatase 213 mU/ml | |

Diagnosis
  Viral heptatis, type "A"
Treatment
  7 drops V-1 orally twice a day
Result
  Complete recovery after 15 days treatment.

| PATIENT 4C | |
|---|---|
| Male: | Age: 8 years |
| Weight: 24 Kgs. | Temperature: 38° C. |

Principal symptoms and signs:

Anorexia, moderate fever of 38° C., Cephalalgia and generally poor condition which was accompanied by muscular pains. After three days there appeared choluria and icteric conjunctivitis accompanied by acholia and hypocholia. Abdominal distention $+$, hepatomegalia painful to the touch $++$, and slight splenomegalia. In laboratory examination the total amount of seral bilirubin was increased. Fever of 38° C., cephalia, anorexia, asthenia and acratia.

| Bilirubin: | direct 3.5 mg/100 ml |
| | indirect 2 mg/100 ml |
| lactic dehydrogenase 467 mU/ml | |
| Transaminase: | glutamic - pyruvic 78 mU/ml |
| | glutamic - oxalacetic 52 mU/ml |
| alkaline phosphatase 174 mU/ml | |

Diagnosis
  Viral hepatitis, type "A" (Infectious)
Treatment
  5 drops V-1 orally twice a day
Result
  Complete recovery after 15 days treatment.

| PATIENT 4D | |
|---|---|
| Male: | Age: 53 years |
| Weight: 72 Kgs. | Temperature: 37.5° C. T.A. 140/80 |

Principal symptoms and signs:

Cephalalgia arteriomuscular pains and generalized urticaria which lasted 10 days, to present choluria which was accompanied by icteric conjunctivitis, hypocholic and acholic. Hepatomegaly painful to the touch $++$, and slight splenamegaly. The amount of bilirubin as well as transaminase were altered. Generally poor condition, asthenia, acratia and anorexia.

| Bilirubin: | direct 7.3 mg/100 ml |
| | indirect 5.2 mg/100 ml |
| lactic dehydrogenase 684 mU/ml | |
| Transaminase: | glutamic - pyruvic 68 mU/ml |
| | glutamic - oxalacetic 57 mU/ml |
| alkaline phosphatase 148 mU/ml | |

Diagnosis
  Viral hepatitis, type "B"
Treatment
  10 drops V-1 orally twice a day
Result
  Complete recovery after 20 days treatment.

| PATIENT 4E | |
|---|---|
| Male: | |
| Age: | 6 years |
| Weight: | 21 Kgs. |

Clinical Diagnosis
  Viral Hepatitis.
Treatment
  4 drops V-1 orally three times daily.
Result
  Complete recovery after 22 days treatment.

| PATIENT 4F | |
|---|---|
| Male: | |
| Age: | 45 years |
| Weight: | 80 kgs |

Clinical Diagnosis
  Viral Hepatitis
Treatment
  8 drops V-1 orally three times daily
Result
  Complete recovery after 16 days treatment.

| PATIENT 4G | |
|---|---|
| Female: | |
| Age: | 31 years |
| Weight: | 56 Kgs. |

Clinical Diagnosis
  Viral Hepatitis.
Treatment
  6 drops V-1 orally three times daily.
Result
  Complete recovery after 22 days treatment.

EXAMPLE 5

Sample Clinical Results (V-1) Genital Herpes

| PATIENT 5A | |
|---|---|
| Male: | |
| Age: | 26 years |
| Weight: | 65 Kgs. |

Clinical Diagnosis
 Genital Herpes
Treatment
 10 drops V-1 orally three times daily.
Result
 Complete recovery after 40 days treatment leaving no scars or marks.

| PATIENT 5B | |
|---|---|
| Female: | |
| Age: | 32 years |
| Weight: | 65 Kgs. |

Clinical Diagnosis
 Genital Herpes
Treatment
 10 drops V-1 orally three times daily.
Result
 Complete recovery after 38 days treatment leaving no scars or marks.

| PATIENT 5C | |
|---|---|
| Male: | |
| Age: | 31 years |
| Weight: | 70 Kgs. |

Clinical Diagnosis
 Genital Herpes
Treatment
 10 drops V-1 orally three times daily.
Result
 Complete recovery after 40 days treatment leaving no scars or marks.

| PATIENT 5D | |
|---|---|
| Male: | |
| Age: | 30 years |
| Weight: | 76 Kgs. |

Clinical Diagnosis
 Genital Herpes
Treatment
 11 drops V-1 orally three times daily.
Result
 Complete recovery after 42 days treatment leaving no scars or marks.

| PATIENT 5E | |
|---|---|
| Female: | |
| Age: | 25 |
| Weight: | 58 Kgs. |

Clinical Diagnosis
 Genital Herpes
Treatment
 9 drops V-1 orally three times daily.
Result
 Patient attended at clinic on following days:
 Day 1—Treatment commenced
 Day 7—No improvement
 Day 14—No improvement
 Day 21—Wounds decreased in size
 Day 28—Wounds healing
 Day 42—Wounds greatly improved and healing rapidly.
 Day 53—Wounds completely dry and without so treatment ceased.

| PATIENT 5F | |
|---|---|
| Male: | |
| Age: | 30 years |
| Weight: | 70 Kgs. |

Clinical Diagnosis
 Genital Herpes
Treatment
 10 drops V-1 orally three times daily.
Result
 Patient attended at clinic on following days:
 Day 1—Treatment commenced
 Day 7—No improvement
 Day 14—No improvement
 Day 21—No improvement
 Day 28—No improvement
 Day 42—Wounds healing rapidly.
 Day 53—Wounds completely dry and treatment ceased.

| PATIENT 5G | |
|---|---|
| Male: | |
| Age: | 28 years |
| Weight: | 64 Kgs. |

Clinical Diagnosis
 Genital Herpes
Treatment
 7 drops V-1 orally three times daily plus direct application of V-1 to affected area every 12 hours.
Result
 Complete recovery after 35 days treatment leaving no scars or marks

| PATIENT 5H | |
|---|---|
| Female: | |
| Age: | 20 years |
| Weight: | 48 kgs. |

Clinical Diagnosis
 Genital Herpes
Treatment
 5 drops V-1 orally three times daily plus direct application of V-1 to affected area every 12 hours.
Result
 Complete recovery after 35 days treatment leaving no scars or marks.

| PATIENT 5I | |
|---|---|
| Male: | |
| Age: | 35 years |
| Weight: | 70 Kgs. |

Clinical Diagnosis
  Genital Herpes
Treatment
  7 drops V-1 orally three times daily plus direct application of V-1 to affected area every 12 hours.
Result
  Complete recovery after 20 days treatment leaving no scars or marks

| PATIENT 5J | |
|---|---|
| Female: | |
| Age: | 26 years |
| Weight: | 54 Kgs. |

Clinical Diagnosis
  Genital Herpes
Treatment
  6 drops V-1 orally three times daily plus direct application of V-1 to affected area every 12 hours.
Result
  Complete recovery after 20 days treatment leaving no scars or marks.
  All of Patents 5A and 5J were checked every 14 days for two months following end of treatment and in all cases there was no sign of return of infection.

EXAMPLE 6

Water (650 ml) is added to sodium metabisulfite (68 gms) in a 1.5 liter vessel. The vessel is closed and the mixture stirred for 10 minutes. In a separate 1 liter vessel, chrysanthemum powder (110 gms; 1.2% concentration) is added to ethyl alcohol (180 proof; 350 ml) and the mixture stirred every six days. The mixture is allowed to macerate for 30 days at room temperature and then filtered. The filtrate (identified as "V-2" has similar medical properties to those of "V-1" but is somewhat less active.

EXAMPLE 7

Sample Clinical Results (V-2)—Genital Herpes

| PATIENT 7A | |
|---|---|
| Female: | |
| Age: | 26 years |
| Weight: | 51 Kgs. |

Clinical Diagnosis
  Genital Herpes
Treatment
  8 drops V-2 orally three times daily
Result
  Wounds completely dry after 43 days treatment.

| PATIENT 7B | |
|---|---|
| Male: | |
| Age: | 21 years |
| Weight: | 68 Kgs. |

Clinical Diagnosis
  Genital Herpes
Treatment
  10 drops V-2 orally three times daily
Result
  Wounds completely dry after 20 days treatment.

| PATIENT 7C | |
|---|---|
| Female: | |
| Age: | 19 |
| Weight: | 46 Kgs. |

Clinical Diagnosis
  Genital Herpes
Treatment
  7 drops V-2 orally three times daily
Result
  Wounds completely dry after 28 days treatment.

| PATIENT 7D | |
|---|---|
| Male: | |
| Age: | 33 years |
| Weight: | 72 Kgs. |

Clinical Diagnosis
  Genital Herpes
Treatment
  11 drops V-2 orally twice daily
Result
  Wounds completely healed without scar after 40 days treatment.

| PATIENT 7E | |
|---|---|
| Female: | |
| Age: | 25 years |
| Weight: | 55 Kgs. |

Clinical Diagnosis
  Genital Herpes
Treatment
  9 drops V-2 orally twice daily
Result
  Wounds completely healed with no scar after 40 day treatment.

| PATIENT 7F | |
|---|---|
| Female: | |
| Age: | 18 years |
| Weight: | 52 Kgs. |

Clinical Diagnosis
  Genital Herpes
Treatment
  8 drops V-2 orally three times daily.
Result
  Patient attended at clinic on following days:
  Day 1—Treatment commenced
  Day 7—No improvement
  Day 15—No improvement
  Day 22—No improvement
  Day 29—No improvement
  Day 36—No improvement
  Day 43—Wounds healing
  Day 57—Wounds completely dry Day 71—No sign of herpetic injury and treatment ceased.

| PATIENT 7G | |
|---|---|
| Male: | |
| Age: | 22 years |
| Weight: | 68 Kgs. |

Clinical Diagnosis
  Genital Herpes
Treatment
  10 drops V-2 orally three times daily.
Result
  Patient attended at clinic on following days:
  Day 1—Treatment commenced
  Day 7—No improvement
  Day 15—No improvement
  Day 22—No improvement
  Day 29—Wounds decreased in size, form and sensitivity
  Day 36—No further improvement
  Day 43—No further improvement
  Day 57—Wounds completely dry
  Day 71—No sign of herpetic injury and treatment ceased.

All of patients 7A to 7G were checked every 14 days for two months following end of treatment and in all cases there was no sign of return of infection.

EXAMPLE 8

Sample Clinical Result (V-2)—Viral Hepatitis

| PATIENT 8 | |
|---|---|
| Male: | |
| Age: | 18 years |
| Weight: | 65 Kgs. |

Clinical Diagnosis
  Viral Hepatitis
Treatment
  7 drops V-2 orally three times daily.
Result
  Complete recovery after 16 days treatment.

EXAMPLE 9

Sample Clinical Results (V-1)—Viral Influenza

| PATIENT 9A | |
|---|---|
| Male: | |
| Age: | 28 years |
| Weight: | 68 Kgs. |

Clinical Diagnosis
  Viral Influenza
Treatment
  7 drops V-1 orally three times daily after meals.
Result
  Complete recovery after 3 days.

| PATIENT 9B | |
|---|---|
| Female: | |
| Age: | 54 years |
| Weight: | 60 Kgs. |

Clinical Diagnosis
  Viral Influenza
Treatment
  6 drops V-1 orally three times daily after meals.
Result
  All symptoms disappeared after three days treatment.

| PATIENT 9C | |
|---|---|
| Male: | |
| Age: | 8 years |
| Weight: | 26 Kgs. |

Clinical Diagnosis
  Viral Influenza
Treatment
  3 drops V-1 orally three times daily after meals.
Result
  All symptoms disappeared after 2 days treatment.

| PATIENT 9D | |
|---|---|
| Female: | |
| Age: | 30 years |
| Weight: | 58 Kgs. |

Clinical Diagnosis
  Viral Influenza
Treatment
  6 drops V-1 orally three times daily after meals.
Result
  All symptoms disappeared after two days treatment.

EXAMPLE 10

Sample Clinical Results (V-1)—Parotitis

| PATIENT 10A | |
|---|---|
| Male: | |
| Age: | 40 years |
| Weight: | 62 Kgs. |

Clinical Diagnosis
  Parotitis
Treatment
  7 drops V-1 orally three times daily.
Result
  Complete recovery after 13 days treatment.

| PATIENT 10B | |
|---|---|
| Male: | |
| Age: | 18 years |
| Weight: | 60 Kgs. |

Clinical Diagnosis
  Parotitis
Treatment
  6 drops V-1 orally three times daily.
Result
  Complete recovery after 8 days treatment.

EXAMPLE 11

Sample Clinical Results (V-2)—Parotitis

| PATIENT 11A | |
|---|---|
| Male: | |
| Age: | 54 years |
| Weight: | 75 Kgs. |

Clinical Diagnosis
  Parotitis
Treatment
  8 drops V-2 orally three times daily.
Result
  Complete recovery after 7 days treatment.

| PATIENT 11B | |
|---|---|
| Female: | |
| Age: | 60 years |
| Weight: | 71 Kgs. |

Clinical Diagnosis
  Parotitis
Treatment
  7 drops V-2 orally three times daily.
Result
  Complete recovery after 13 days treatment.

EXAMPLE 12

Sample Clinical Result (V-1)—Herpes Zoster

| PATIENT 12 | |
|---|---|
| Male: | |
| Age: | 58 years |
| Weight: | 78 Kgs. |

Clinical Diagnosis
  Herpes Zoster infection having small (1–5 mm) red blisters in the intercostal region grouped in the form of an erythema. Intense pain at palpation, paresthesia, cutaneous hiperesthesia and itching.
Treatment
  8 drops V-1 orally three times daily plus direct application of V-1 in affected area every twelve hours.
Result
  Complete recovery after 37 days treatment.

I claim:

1. A method of treating a parasitic disease selected from amoebiasis, malaria and trichomoniasis which comprises orally administering to a patient suffering the disease, an effective amount of a pyrethroid at a dose in the range 0.0001 mg/kg to 1 mg/kg body weight one to four times daily.

2. The method claimed in claim 1 wherein alpha-pinene is administered concomitantly with the pyrethroid.

3. The method as claimed in claim 1 wherein the pyrethroid is administered at a dose in the range 0.01 to 0.1 mg/kg body weight one to four times daily.

4. The method claimed in claim 1, wherein the pyrethroid is selected from an extract of pyrethrum with water, an extract of pyrethrum with ethyl alcohol, and an extract of pyrethrum with alpha-pinene.

5. The method claimed in claim 1 wherein the disease treated is amoebiasis.

6. The method claimed in claim 1 wherein the disease treated is malaria.

7. An oral pharmaceutical composition in unit dosage form consisting essentially of a pyrethroid in admixture or otherwise associated with a pharmaceutically acceptable diluent or carrier and containing 0.0005 mg to 5 mg of the pyrethroid per unit dose.

8. The composition claimed in claim 7 which is selected from an aqueous solution of the pyrethroid, a solution of the pyrethroid in aqueous ethyl alcohol, and a solution of the pyrethroid in alpha-pinene.

9. The composition claimed in claim 7 which also contains sodium metabisulphite.

10. The composition claimed in claim 7 containing 0.01 to 1 mg of pyrethroid per unit dose.

11. The composition claimed in claim 7 which is a solution of the pyrethroid in a liquid carrier wherein the concentration of pyrethroid is 0.001 to 1 percent by weight.

12. The composition claimed in claim 11 which is a solution of 0.1 to 0.5 percent by weight pyrethroid in alpha-pinene.

13. The composition claimed in claim 12 which is obtained by macerating pyrethrum in turpentine optionally containing up to 11% sodium metabisulphite.

14. The composition claimed in claim 11 which is a solution of 0.001 to 1.0 percent by weight of the pyrethroid in aqueous ethyl alcohol.

15. The composition claimed in claim 14 which is obtained by homogenizing an ethyl alcohol extract of pyrethrum with aqueous ethyl alcohol optionally containing up to 11% sodium metabisulphite.

* * * * *